(12) United States Patent
Takada et al.

(10) Patent No.: US 6,960,461 B2
(45) Date of Patent: Nov. 1, 2005

(54) GENE CODING FOR CYCLODEXTRIN GLUCANOTRANSFERASE CHIEFLY PRODUCING γ-CYCLODEXTRIN AND USE THEREOF

(75) Inventors: Masayasu Takada, Fuji (JP); Takahiro Ide, Fuji (JP); Yoshinori Nakagawa, Fuji (JP); Takeshi Yamamoto, Sapporo (JP); Mikio Yamamoto, Fuji (JP)

(73) Assignee: Nihon Shokuhin Kako Co., Ltd., Tokyo (JP)

( * ) Notice: Subject to any disclaimer, the term of this patent is extended or adjusted under 35 U.S.C. 154(b) by 178 days.

(21) Appl. No.: 10/188,066

(22) Filed: Jul. 3, 2002

(65) Prior Publication Data

US 2003/0114417 A1 Jun. 19, 2003

(30) Foreign Application Priority Data

Jul. 11, 2001 (JP) .......................... 2001-211340

(51) Int. Cl.[7] .............. C12N 9/00; C12N 9/46; C07H 21/04
(52) U.S. Cl. .................. 435/211; 435/4; 435/6; 435/69.1; 435/183; 435/200; 435/252.3; 435/320.1; 530/350; 536/23.2; 536/23.5; 536/23.7
(58) Field of Search ................ 435/4, 6, 69.1, 435/183, 200 T, 211, 252.3, 320.1; 536/23.2 T, 23.5, 23.7

(56) References Cited

FOREIGN PATENT DOCUMENTS

| EP | 0 630 967 A1 | 6/1994 |
| EP | 0 614 971 A2 | 9/1994 |
| EP | 0 802 259 A1 | 4/1997 |
| WO | WO 91/14770 | 10/1991 |
| WO | WO 96 33267 | 10/1996 |
| WO | WO 01/90335 A1 | 11/2001 |

OTHER PUBLICATIONS

Schmid G. (GenBank Accession No. AAR14202, 1991).*
Parsiegla et al., "Substrate binding to a cyclodextrin glycosyltransferase and mutations increasing the Γ–cyclodextrin production", XP–002223754, European Journal of Biochemistry, vol. 255. No. 3, (Aug. 1998), pp. 710–717.

Nitschke et al., "Molecular cloning, nucleotide, sequence and expression in Escherichia coli of the β–cyclodextrin glycosyltransferase gene from Bacillus circulans strain No. 8", XP–000676776, Applied Microbiology and Biotechnology, Springer Verlag, Berlin, DE, vol. 33, No. 5, (Aug. 1990), pp. 542–546.

Kato et al., "Cloning and Expression of the Bacillus subtilis No. 313 Γ–Cyclodextrin Forming CGTase Gene in Escherichia coli", XP–009002198, Agricultural and Biological Chemistry, vol. 50, No. 8, (1986), pp. 2161–2162.

Fujiwara et al., "Cyclization Characteristics of Cyclodextrin Glucanotransferase Are Conferred by the $NH_2$–Terminal Region of the Enzyme", XP–000676761, Applied and Environmental Microbiology, Washington, DC, US, vol. 58, No. 12 (Dec. 1992) pp. 4016–4025.

Sin et al., "Replacement of an amino acid residue of cyclodextrin glucanotranferase of Bacillus ohbensis doubles the production of Γ–cyclodextrin", XP–002034110, Journal of Biotechnology, Elsevier Science Publishers, vol. 32, No. 3, (Feb. 1994), pp. 283–288.

* cited by examiner

Primary Examiner—Manjunath N. Rao
(74) Attorney, Agent, or Firm—Jacobson Holman PLLC

(57) ABSTRACT

The invention provides a gene (isolated nucleic acid molecule) encoding the cyclodextrin glucanotransferase which produces a considerable amount of γ-cyclodextrin (γ-CD) from the substrates selected from among starch and starch decomposition products such as dextrin, amylopectin and amylose; recombinant plasmids comprising this gene; transformants transformed with the recombinant plasmid; methods of manufacturing the cyclodextrin glucanotransferase by employing these transformants to act upon the substrates selected from among starch and decomposition products thereof and causing the production of γ-CD as a main product; and methods of manufacturing γ-CD and CD-comprising compositions having a desired CD balance (α-, β- and γ-CD balance) employing this recombinant cyclodextrin glucanotransferase.

5 Claims, 3 Drawing Sheets

GENE CODING FOR CYCLODEXTRIN GLUCANOTRANSFERASE CHIEFLY PRODUCING γ-CYCLODEXTRIN AND USE THEREOF

BACKGROUND OF THE INVENTION

1. Field of the Invention

The present invention relates to a gene (isolated nucleic acid molecule) encoding the cyclodextrin glucanotransferase which produces a considerable amount of γ-cyclodextrin (γ-CD) from the substrates selected from among starch and starch decomposition products such as dextrin, amylopectin and amylose; recombinant plasmids comprising this gene; transformants transformed with the recombinant plasmid; methods of manufacturing the cyclodextrin glucanotransferase by employing these transformants to act upon the substrates selected from among starch and decomposition products thereof and causing the production of γ-CD as a main product; and methods of manufacturing γ-CD and CD-comprising compositions having a desired CD balance (α-, β- and γ-CD balance) employing this recombinant cyclodextrin glucanotransferase.

2. Description of Related Art

Cyclodextrin glucanotransferase (CGTase; EC 2.4.1.19) is an enzyme that acts on α-1,4-glucans such as starch and produces cyclodextrins (CDs), a cyclic α-1,4-glucan, by intermolecular transglycosylation activity. CDs composed of 6, 7 and 8 D-glucosyl moieties are called as α-, β- and γ-CD respectively. Aside from this CD-producing reaction, through intermolecular transglycosylation, CGTase also catalyzes coupling reactions (reactions in which the CD ring is opened and the straight-chain oligosaccharides produced are transferred to receptor sugar molecules) and disproportionation reactions (in which straight-chain oligosaccharides are transferred to receptor sugar molecules). Further, CGTase also weakly catalyzes hydrolysis of α-1,4-glucoside bonds. These CDs are interesting molecules from the viewpoints of food and medical applications and so on, because of their ability to from inclusion complexes with many organic and inorganic molecules, thereby changing the physical and chemical properties. (E. B. Tilden and S. J. Pirt, J. Am. Chem. Soc., 63, 2900–2902, 1939). Significant research has been conducted, including the search for CGTase-producing bacteria and the purification of the enzyme since the synthesis of CDs by the CGTase from *Bacillus macerans* was reported in 1939 (Sumio Kitahata, Naoto Tsuyama and Shigetaka Okada, Agr. Biol. Chem., 38 (2), 387–393, 1974; Sumio Kitahata and Shigetaka Okada, Agr. Biol. Chem., 38 (12), 2413–2417, 1974; Sumio Kitahata and Shigetaka Okada, J. Jap. Soc. Starch Sci., 29 (1), 13–18, 1982; Michio Kubota, Yoshiki Matsuura, Shuzo Sakai and Yukiteru Katsube, Denpun Kagaku, 38 (2), 141–146, 1991; Lionel J. Bovetto, Daniel P. Backer, Jaques R. Villette, Philippe J. Sicard, and Stephane J-L. Bouquelet, Biotechnology and Applied Biochemistry, 15, 48–58, 1992; Shinske Fujiwara, Hirofumi Kakihara, Kim Myung Woo, Andre Lejeune, Mitsuhide Kanemoto, Keiji Sakaguchi, and Tadayuki Imanaka, Applied and environmental microbiology, 58 (12), 4016–4025, 1992; Florian Binder, Otto Huber and August Bock, Gene, 47, 269–277, 1986; Keiji Kainuma, Toshiya Takano and Kunio Yamane, Appl. Microbiol. Biotechnol., 26, 149–153, 1987; Takahiro Kaneko, Tetsuo Hamamoto and Koki Horikoshi, J. general Microbiology, 134, 97–105, 1988; Murai Makela, Pekka Mattsson, M. Eugenia Schinina, and Timo Korpela, Biotechnology and Applied biochemistry, 10, 414–427, 1988; and Ernest K. C. Yu, Hiroyuki Aoki, and Masanaru Misawa, Appl. Microbiol. Biotechnol., 28, 377–379, 1988).

CGTases are classified into α-, β- and γ-CGTase depending on the main products of CD. Most reports have dealt with α- and β-CGTase; there are few enzymes reported to be γ-CGTase (Shigeharu Mori, Susumu Hirose, Takaichi Oya, and Sumio Kitahata, Oyo Toshitsu Kagaku, 41 (2), 245–253, 1994; Yoshito Fujita, Hitoshi Tsubouchi, Yukio Inagi, Keiji Tomita, Akira Ozaki, and Kazuhiro Nakanishi, J. Fermentation and Bioengineering, 70 (3), 150–154, 1990; Takashi Kato and Koki Horikoshi, J. Jpn. Soc. Starch Sci., 33 (2), 137–143, 1986). Further, of those enzymes reported as γ-CGTase, the γ-CD production yield is less than 5 percent; an amount of β-CD that is equal to or greater than the amount of γ-CD is produced since the rate of production of β-CD is accelerated in the late stage of reaction; or the γ-CD production rate decreases sharply at a substrate concentration of 10 percent or more. Still further, these enzymes do not lend themselves to an industrial use since they requires countermeasures such as the addition of ethanol to the reaction solution.

Some attempts to improve the amount of γ-CD produced by modifying the structural gene of α- or β-CGTase have been reported (Akira Nakamura, Keiko Haga, and Kunio Yamane, Biochemistry, 32, 6624–6631, 1993; Michio Kubota, Yoshiki Matsuura, Shuzo Sakai and Yukiteru Kutsume, Oyo Toshitsu Kagaku, 41 (2), 245–253, 1994). However, even when the amount of γ-CD produced increases, the amount of β-CD produced by the original activity does not markedly decrease, which is inadequate from an industrial perspective. As a result, although α-CD and β-CD are employed in various fields, γ-CD is hardly employed at all. The same is true of CD-comprising compositions. CD-comprising compositions containing α- or β-CD as a main product are employed in a great many fields, but CD-comprising compositions containing γ-CD as a main product are hardly employed at all. In CD-comprising compositions, the CGTase employed to prepare the compositions ends up determining the CD composition based on α-, β-, or γ-CGTase, and it is difficult to prepare a CD-comprising composition having a desired CD balance.

In light of this state of the art, the present inventors previously discovered that *Bacillus clarkii* 7364 produces a new γ-CGTase producing γ-CD as a main product, employed this enzyme to develop a method of manufacturing γ-CD and a CD-comprising composition of desired CD balance, and applied for patents (Japanese Patent Application Un-examined Publication Nos. 2001-327299 and 2001-327284).

However, these microbes do not afford adequate enzyme productivity. When γ-CD and CD-comprising compositions of desired CD balance are prepared on an industrial scale, there is a problem in that the microbe must be cultured on a large scale. Conventionally, to solve this problem, wild strains have been bred in a complex manner using ultraviolet radiation, X-rays, and reagents such as NTG (N-methyl-N'-nitro-N-nitrosoguanidine) and EMS (ethylmethane sulfonate) to create mutant strains having improved enzyme productivity. Further, microbes producing CGTase often produce trace amounts of α-amylase at the same time as CGTase. Thus, when causing CGTase to act upon substrates selected from among starch and decomposition products thereof to produce γ-CD as a main product, the yield is reduced due to hydrolysis of the γ-CD by α-amylase that is present in the crude enzyme. One conceivable method of solving this problem is to purify the crude enzyme and remove the α-amylase. However, in that case, there is a problem of high enzyme production costs. A further method is to inhibit the expression of the amylase gene by an artificial method and relatively increase CGTase activity. However, in this method, it is often difficult to obtain mutant strains in which α-amylase activity alone is selectively inhibited.

It has currently become possible to readily obtain the gene encoding a useful enzyme, create recombinant DNA comprising the gene, and introduce it into a microbe to relatively easily obtain a desired level of enzyme.

Based on this state of the art, the technique of locating the gene encoding γ-CGTase, analyzing the genetic sequence thereof, and improving the productivity and activity of the enzyme by means of transformants into which the gene has been introduced is quite important. Further, once the gene is obtained, mutants can be created to obtain a highly active enzyme. Further, it is anticipated that the techniques of protein engineering can be employed to obtain enzymes with greater heat resistance, pH resistance, and reaction rates.

Accordingly, an object of the present invention is to provide a gene encoding the cyclodextrin glucanotransferase which produces γ-CD as a main product from the substrates selected from among starch and decomposition products thereof, recombinant plasmids comprising this gene and transformants transformed with the recombinant plasmid; a method employing these transformants to manufacture cyclodextrin glucanotransferase acting upon the substrates selected from among starch and decomposition products thereof to producer γ-CD as a main product; and a method employing this recombinant cyclodextrin glucanotransferase to manufacture γ-CD and a CD-comprising composition having a desired CD balance (α-, β-, and γ-CD balance).

SUMMARY OF THE INVENTION

The present inventors screened the microorganisms which produce a new γ-CGTase, producing primarily γ-CD from starch, resulting in the discovery that alkalophilic bacteria classified as the genus *Bacillus* produce the desired γ-CGTase (Japanese Patent Application Un-examined Publication Nos. 2001-327299 and 2001-327284). The alkalophilic *bacillus* isolated from a starch decomposition solution was designated as *Bacillus clarkii* 7364 and deposited it as FERM BP-7156 with the International Patent Organism Depositary (IPOD).

As a result of further intensive research, the present inventors succeeded in isolating the γ-CGTase gene of this microbial strain and successfully expressed it in other microbes such as *E. coli*. The present invention was devised on the basis of these discoveries.

The present invention relates to DNA encoding a protein having the amino acid sequence of amino acid residues 1 to 702 denoted by SEQ ID No. 2 in the attached Sequence Listing, or an amino acid sequence consisting of said amino acid sequence in which one or multiple amino acids have been substituted, inserted, added or deleted; and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 1).

The present invention further relates to DNA encoding a protein having the amino acid sequence of amino acid residues 29 to 702 denoted by SEQ ID No. 2 in the attached Sequence Listing, or an amino acid sequence consisting of said amino acid sequence in which one or multiple amino acids have been substituted, inserted, added or deleted; and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 2).

The present invention further relates to DNA having the nucleotide sequence of nucleotides 321 to 2,426 or the nucleotide sequence of nucleotides 405 to 2,426 of SEQ ID No. 1 of the attached Sequence Listing (Claim 3).

The present invention further relates to DNA hybridizing under stringent conditions with DNA comprised of a nucleotide sequence that is complementary to the DNA described in any of claims 1–3 and encoding a protein having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 4).

With the DNA of claims 1–3, the DNA is preferably derived from a bacterium of the genus *Bacillus* (claim 5) and with the DNA of claim 5, the bacterium of the genus *Bacillus* is *Bacillus clarkii* strain 7364 (FERM BP-7156) (Claim 6).

The present invention further relates to a recombinant plasmid comprising the DNA of any one of claims 1–6 (Claim 7).

The present invention further relates to a transformant obtained by transformation using the plasmid of claim 7 (Claim 8).

The present invention further relates to a transformant in the form of *E. coli* transformed by the plasmid of claim 7 (Claim 9).

The present invention further relates to a method of manufacturing protein comprising culturing the transformant described in claim 8 or 9 and collecting a protein having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 10).

The present invention further relates to a protein having the amino acid sequence of amino acid residues 1 to 702 denoted by SEQ ID No. 2 in the Sequence Listing, or an amino acid sequence consisting of said amino acid sequence in which one or multiple amino acids have been substituted, inserted, added or deleted; and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 11).

The present invention further relates to a protein having the amino acid sequence of amino acid residues 29 to 702 denoted by SEQ ID No. 2 in the Sequence Listing, or an amino acid sequence consisting of said amino acid sequence in which one or multiple amino acids have been substituted, inserted, added or deleted; and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 12).

The present invention further relates to a protein encoded by a nucleotide hybridizing under stringent conditions with DNA having a complementary nucleotide sequence to the DNA described in any of claims 1–3 and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced (Claim 13).

The present invention further relates to a method of manufacturing a composition comprising α-, β-, and γ-cyclodextrin wherein the protein having cyclodextrin glucanotransferase activity described in any one of claims 11–13 and cyclodextrin glucanotransferase having higher β- and γ-cyclodextrin producing activity than γ-cyclodextrin producing activity are simultaneously reacted with a solution comprising at least one from among the group consisting of starch, dextrin, amylopectin and amylose to produce α-cyclodextrin, β-cyclodextrin, and γ-cyclodextrin (Claim 14).

The present invention further relates to a method of manufacturing a composition comprising α-, β-, and γ-cyclodextrin wherein with a solution comprising at least one from among the group consisting of starch, dextrin, amylopectin and amylose, the protein having cyclodextrin glucanotransferase activity described in any one of claims 11–13 is reacted and then cyclodextrin glucanotransferase having higher β- and α-cyclodextrin producing activity than γ-cyclodextrin producing activity is reacted to produce α-cyclodextrin, β-cyclodextrin, and γ-cyclodextrin (Claim 15).

The present invention further relates to a method of manufacturing a composition comprising α-, β-, and γ-cyclodextrin wherein with a solution comprising at least one from among the group consisting of starch, dextrin, amylopectin and amylose, cyclodextrin glucanotransferase having higher β- and α-cyclodextrin producing activity than γ-cyclodextrin producing activity is reacted, and then the protein having cyclodextrin glucanotransferase activity described in any one of claims 11–13 is reacted to produce α-cyclodextrin, β-cyclodextrin, and γ-cyclodextrin (Claim 16).

With the manufacturing method of any of claims 14–16, the reaction conditions are preferably set so that when the quantity of γ-cyclodextrin produced is denoted as 1, the quantity of α-cyclodextrin produced falls within the range of 0.1–2 and the quantity of β-cyclodextrin produced falls within the range of 0.1–2 (Claim 17).

With the manufacturing method of any of claims 14–16, the reaction conditions are preferably set so that when the quantity of α-cyclodextrin produced is denoted as 1, the quantity of β-cyclodextrin produced falls within the range of 0.1–1.5 and the quantity of γ-cyclodextrin produced falls within the range of 0.1–2 (Claim 18).

Figure 1:
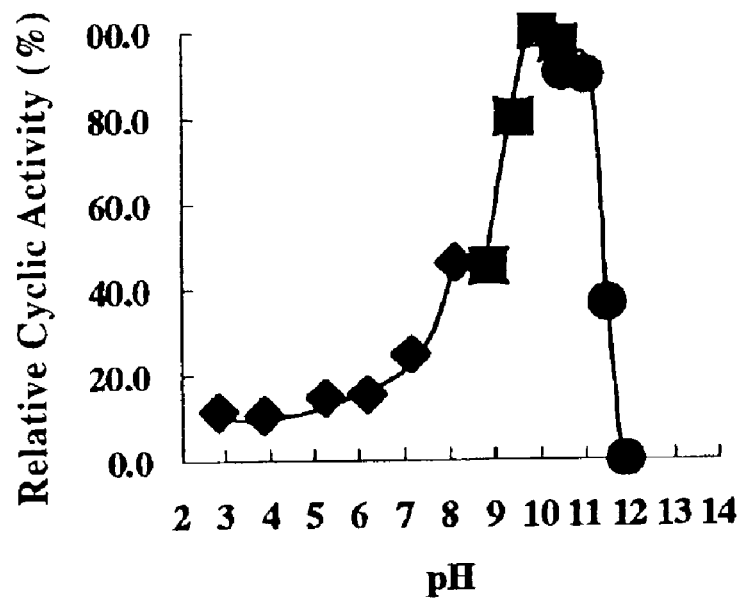
FIG. 1 shows the effects of pH on γ-CGTase cyclic activity by the BCG method.

The protein described in claim 11 has the amino acid sequence indicated by amino acid residues 1 to 702 in SEQ ID No. 2 of the attached Sequence Listing. Further, the protein described in claim 11 has the amino acid sequence indicated by amino acid residues 1 to 702 in SEQ ID No. 2 of the sequence table in which one or multiple amino acids have been substituted, inserted, added or deleted; and has cyclodextrin glucanotransferase activity on starch, dextrin, amylopectin or amylose and produces γ-cyclodextrin as a main product, with the quantity of β- and α-cyclodextrin produced being lower than the quantity of γ-cyclodextrin produced.

The protein described in claim 12 has the amino acid sequence indicated by amino acid residues 29 to 702 in SEQ ID No. 2 of the attached Sequence Listing. Further, the protein described in claim 12 has the amino acid sequence indicated by amino acid residues 29 to 702 in SEQ ID No. 2 of the attached Sequence Listing in which one or multiple amino acids have been substituted, inserted, added or deleted; and has cyclodextrin glucanotransferase activity on starch, dextrin, amylopectin or amylose and produces γ-cyclodextrin as a main product, with the quantity of β- and α-cyclodextrin produced being lower than the quantity of γ-cyclodextrin produced.

In the amino acid sequence of SEQ ID No. 2, the amino acid sequence denoted by amino acid residues 1 to 28 relates to a signal peptide and the amino acid sequence denoted by amino acid residues 29 to 702 relates to a protein which is a mature enzyme (cyclodextrin glucanotransferase). Accordingly, the protein described in claim 11 comprises a signal peptide and a protein of a mature enzyme (cyclodextrin glucanotransferase), and the protein of claim 12 comprises only the enzymatic protein. However, both the protein described in claim 11 and that described in claim 12 have cyclodextrin glucanotransferase activity on starch, dextrin, amylopectin or amylose and produce γ-cyclodextrin as a main product, with the quantity of β- and α-cyclodextrin produced being lower than the quantity of γ-cyclodextrin produced.

Further, the protein described in claim 11 and the protein described in claim 12 may each have an amino acid sequence in which one or multiple amino acids has been substituted, inserted, added or deleted. The location and type of amino acid that is substituted, inserted, added or deleted is not specifically limited. It suffices for the protein to have cyclodextrin glucanotransferase activity on starch, dextrin, amylopectin or amylose and produce γ-cyclodextrin as a main product, with the quantity of β- and α-cyclodextrin produced being lower than the quantity of γ-cyclodextrin produced despite the substitution, insertion, addition, or deletion of one or more amino acids.

The term "amino acid insertion" refers to the addition of a new amino acid in a prescribed amino acid sequence. The term "amino acid addition" refers to the addition (appending) of a new amino acid outside a prescribed amino acid sequence. Cyclodextrin glucanotransferase activity (γ-cyclodextrin producing activity and β- and α-cyclodextrin producing activity) will be described further below.

The DNA described in claim 1 encodes the protein described in claim 11. Further, the DNA described in claim 2 encodes the protein described in claim 12.

The DNA having the nucleotide sequence of nucleotides 321 to 2,426 of SEQ ID No. 1 in the attached Sequence Listing that is described in claim 3 encodes the amino acid sequence denoted by amino acid residues 1 to 702 in SEQ ID No. 2 of the attached Sequence Listing. The DNA having the nucleotide sequence of nucleotides 405 to 2,426 of SEQ ID No. 1 in the attached Sequence Listing that is described in claim 3 encodes the amino acid sequence denoted by amino acid residues 29 to 702 in SEQ ID No. 2 of the attached Sequence Listing. The DNA encoding the amino acid sequence corresponding to the signal peptide has the nucleotide sequence of nucleotides 321–404 in SEQ ID No. 1 of the attached Sequence Listing.

The protein described in claim 13 is a protein encoded by a nucleotide hybridizing under stringent conditions with DNA having a nucleotide sequence complementary to the DNA described in any of claims 1–3 and having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced. The DNA described in claim 4 is DNA encoding the protein described in claim 13.

The term "hybridizing under stringent conditions" employed in the present invention means hybridization under more intense conditions than the Southern hybridization treatment conditions described in the Examples. Specifically, either the concentration of constituent components is higher, the hybridization temperature is higher, the concentration of constituent components in the washing solution is lower, or the washing solution temperature is higher than in the hybridization solution in the Examples; only one of these conditions need be met.

Generally, in double-strand DNA, a heat or alkali treatment will cause the hydrogen bonds to dissociate, yielding single strands (denaturation). Gradually lowering the temperature slowly regenerates double-strand DNA. This denaturation and regeneration is such that denaturation becomes more difficult and regeneration easier the greater the homology of the two strands of DNA. Accordingly, when two different types of double-strand DNA are present and denaturation is conducted followed by regeneration to produce heterogeneous DNA, double-strand DNA is formed in a manner dependent on the level of homology between the sequences. The use of this method to check the homology between different DNAs is called hybridization. The DNA of the present invention covers DNA (but is limited to DNA encoding proteins having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced) having a nucleotide sequence that will hybridize under stringent conditions with DNA having nucleotide sequences complementary to genes encoding amino acid sequences (the amino acid sequence itself or the amino acid sequence with the substitution, inserting, addition, or deletion of one or more amino acid sequences) essentially identical to the amino acid sequence denoted by amino acid residues 1 to 702 in SEQ ID No. 2 or amino acid residues 29 to 702 in SEQ ID No. 2. When conducted under stringent conditions, DNA having high homology with the structural gene of γ-CGTase can be efficiently selected. From among that DNA, DNA encoding proteins having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced, can be suitably selected by the usual methods based on protein having cyclodextrin glucanotransferase activity to obtain the DNA described in claim 4 and the protein described in claim 13.

The DNA described in claims 1–3 can be DNA derived from bacteria of the genus Bacillus. The bacterium classified as the genus Bacillus can be Bacillus clarkii strain 7364 (FERM BP-7156). However, all DNA described by claims 1–3 is covered under the present invention irrespective of the source thereof.

The present invention also covers recombinant plasmids comprising the DNA described in any of claims 1 to 6. The vector used to incorporate the DNA described in any of claims 1 to 6 is not specifically limited. Types of vectors and promoters will be described further below. The insertion of the DNA described in any of claims 1 to 6 into such a vector can be suitably accomplished by one of the known methods.

The present invention further covers transformants obtained by transforming the above-mentioned recombinant plasmids. One example of a bacterium suitable for transformation is E. coli. Hosts other than E. coli will be described further below. The transformation of bacteria can be suitably conducted by known methods.

The present invention further covers methods of manufacturing proteins comprising the step of culturing the above-described transformant of the present invention, and the step of collecting protein having cyclodextrin glucanotransferase activity on starch, dextrin, amylopectin or amylose and producing γ-cyclodextrin as a main product, with the quantity of β- and α-cyclodextrin produced being lower than the quantity of γ-cyclodextrin produced. The transformant can be suitably cultured by a known method based on the type of bacteria from which the transformant originated. Further, the protein can be collected by the usual methods. The protein that is collected can be suitably purified or the like.

In the first method of manufacturing CD compositions of the present invention, the recombinant protein of the present invention in the form of CGTase and cyclodextrin glucanotransferase with a β- and α-cyclodextrin producing activity greater than γ-cyclodextrin producing activity (specifically, CGTase produced by a bacterial strain other than Bacillus clarkii) are simultaneously reacted with a solution (starting material solution) comprising at least one member selected from the group consisting of starch, dextrin, amylopectin and amylose to produce α-CD, β-CD, and γ-CD.

CGTase produced by a bacterial strain other than Bacillus clarkii in the form of cyclodextrin glucanotransferase having greater β- and α-cyclodextrin producing activity than γ-cyclodextrin producing activity is described below.

In the present invention, CGTase produced by a bacterial strain other than Bacillus clarkii is CGTase that produces α- and/or β-CD with preference over γ-CD. Examples of such CGTase produced by bacterial strains other than Bacillus clarkii are one or more selected from among the group consisting of: cyclodextrin glucanotransferase derived from the genus Bacillus, cyclodextrin glucanotransferase derived from klebsiella, cyclodextrin glucanotransferase derived from Thremoanaerobactor, and cyclodextrin glucanotransferase derived from Brevibacterium. Examples of such CGTase are the Bacillus sp. AL-6, Bacillus stearothermophilus, Bacillus megaterium, Bacillus circulans, and Bacillus macerans indicated in Table 1 below, as well as the Bacillus ohbensis, Klebsiella pneumoniae, Thermoana erobactor sp., and Brevibacterium sp. No. 9605 indicated in Table 1 below.

TABLE 1

|  | B. ohbensis | Klebsiella pneumoniae | Thermoana erobactor sp. | Brevibacterium sp. No. 9605 |
|---|---|---|---|---|
| Isoelectric point | <4 | — | 6.3–6.7 | 2.8 |
| Optimum pH | 5.5 | 5.2 | 5.0–6.5 | 10 |
| Optimum temp. | 60° C. |  | 90–95° C. | 45° C. |
| Stability (pH) | 6.5–9.5 | 6.0–7.5 | — | 6.0–8.0 |
| Stability (temp) | 55° C. | 45° C. | 75° C. | 50° C. |
| Molecular weight | 35,000 |  |  | 75,000 |
| Principal product | β | α | α, β | γ, β |

In the first method of manufacturing a CD composition of the present invention, concentrations in the starting material solution of, for example, 1–30 percent and 0.05–300 U (per gram of dry starch) of each CGTase are employed. The enzymatic reaction is conducted within a pH range of 4.5–12 and a temperature of 20–75° C. for 1–96 hours to produce a composition comprising α-CD, β-CD, and γ-CD.

In the second method of manufacturing a CD composition of the present invention, CGTase, the recombinant protein of the present invention, is reacted with a starting solution comprising at least one member selected from the group consisting of starch, dextrin, amylopectin and amylose, after which CGTase produced by a bacterial strain other than *Bacillus clarkii* is reacted to produce α-CD, β-CD, and γ-CD. The concentration of the starting material solution is, for example, 1–30 percent. The CGTase is added to the starting material solution in a quantity of 0.05–300 U (per gram of dry starch) and the enzymatic reaction is conducted for 1–96 hours within a pH range of 4.5–12 and a temperature of 20–75° C. Next, the reaction solution is heated to inactivate the CGTase of the present invention, after which 0.05–300 U (per gram of dry starch) of CGTase produced by a bacterial strain other than *Bacillus clarkii* is added to the reaction solution. The enzymatic reaction is then conducted for 1–96 hours at a pH of 4.5–12 and a temperature of 20–75° C. to produce a composition comprising α-CD, β-CD, and γ-CD.

In the third method of manufacturing a CD composition of the present invention, CGTase produced by a strain of bacteria other than *Bacillus clarkii* is reacted with a starting material solution comprising at least one member selected from among the group consisting of starch, dextrin, amylopectin and amylose. Next, CGTase, the recombinant protein of the present invention, is reacted to produce α-CD, β-CD and γ-CD.

The concentration of the starting material solution is, for example, 1–30 percent. CGTase produced by a bacterial strain other than *Bacillus clarkii* is added to the starting material solution in a quantity of 0.05–300 U (per gram of dry starch) and the enzymatic reaction is conducted within a pH range of 4.5–12 and at a temperature of 20–75° C. for 1–96 hours. Next, the reaction solution is heated to inactivate the CGTase produced by a bacterial strain other than *Bacillus clarkii* is added to the reaction solution in a quantity of 0.05–300 U (per gram of dry starch), and the enzymatic reaction is conducted within a pH range of 4.5–12 and at temperature of 20–75° C. for 1–96 hours to produce a composition comprising α-CD, β-CD, and γ-CD.

The reaction conditions (quantity of enzyme employed, reaction time, reaction temperature, and the like) can be set so that when the quantity of γ-CD produced is denoted as 1, the quantity of α-CD produced falls within the range of 0.1–2 and the quantity of β-CD produced falls within the range of 0.1–2. Preferably, the reaction conditions are set so that when the quantity of γ-CD produced is denoted as 1, the quantity of α-CD produced falls within the range of 0.1–1 and the quantity of β-CD produced falls within the range of 0.1–0.5. The reaction conditions (quantity of enzyme employed, reaction time, reaction temperature, and the like) can also be set so that when the quantity of α-CD produced is denoted as 1, the quantity of β-CD produced falls within the range of 0.1–1.5 and the quantity of γ-CD produced falls within the range of 0.1–2. Preferably, the reaction conditions are set so that when the quantity of α-CD produced is denoted as 1, the quantity of β-CD produced falls within the range of 0.3–0.9 and the quantity of γ-CD produced falls within the range of 0.5–1.

In the first method of manufacturing a CD composition of the present invention, the ratio of each of the CDs produced and the ratio of the quantities produced can be varied by changing (i) the ratio of the quantity of CGTase produced by a bacterial strain other than *Bacillus clarkii* that is employed to the quantity of recombinant protein of the present invention in the form of CGTase that is employed; (ii) by choosing the reaction temperature close to the optimum temperature of either of the CGTases when the optimum temperature of the CGTase varies with the type of CGTase.

In the second method of manufacturing a CD composition of the present invention, the conditions (quantity of enzyme employed, reaction temperature, reaction time) used to produce CD the primary component of which is γ-CD based on the recombinant protein of the present invention in the form of CGTase and the conditions (quantity of enzyme employed, reaction temperature, reaction time) used to produce CDs the chief components of which are α- and/or β-CD based on CGTase produced by a bacterial strain other than *Bacillus clarkii* can be varied to change the ratio of quantities produced.

In the third method of manufacturing a CD composition of the present invention, the conditions (quantity of enzyme employed, reaction temperature, reaction time) used to produce CDs the chief components of which are α- and/or β-CD based on CGTase produced by a bacterial strain other than *Bacillus clarkii* and the conditions (quantity of enzyme employed, reaction temperature, reaction time) used to produce CD the chief component of which is γ-CD based on the recombinant protein of the present invention in the form of CGTase can be varied to change the ratio of quantities produced.

The solution comprising a mixture of α-, β-, and γ-CDs obtained by the methods of manufacturing CD compositions of the present invention can be further purified to obtain a mixed cyclodextrin syrup. This purification can be conducted by the same methods used for common thick malt syrups and oligosaccharide syrups. For example, this purification can be conducted by suitably combining filtration to remove solid components, decoloring by treatment with activated charcoal, and desalting with ion-exchange resin. Further, the compositions containing the α-, β-, and γ-CDs obtained by the manufacturing methods of the present invention sometimes contain monosaccharides such as glucose, various oligosaccharides (maltose and the like), and dextrin in addition to α-, β-, and γ-CDs. These can be suitably separated by the usual methods.

Once the reaction solution containing the composition comprising α-, β-, and γ-CDs obtained by the manufacturing method of the present invention has been purified in the manner set forth above to obtain a cyclodextrin mixed syrup, the syrup can be dried to obtain a powder of mixed cyclodextrins. The syrup can be dried by spray drying or freeze drying. Depending on the drying method, various forms of product such as crystals, freeze-dried produce, powder, granules, or the like can be obtained.

The present invention is described in detail below.

The γ-CGTase Gene

As stated above, the γ-CGTase gene based on the present invention is a DNA sequence encoding a protein acting on the substrates selected from among starches and their decomposition products and having cyclodextrin glucanotransferase activity causing the production principally of γ-CD. Based on amino acid sequence information of the γ-CGTase portion, the gene encoding the enzyme was successfully obtained by PCR employing chromosomal DNA of bacteria producing that enzyme (*Bacillus clarkii* strain 7364) as a template. This gene was also determined by successful expression in microbes such as *E. coli*.

1) Deposit of Microbes

The *E. coli* bacterium JM109 expressing in large quantity the γ-CGTase of the present invention that has been transformed with the classical gene-comprising plasmid pGFT-01 of the present invention (see the Examples described below) was named GCG31 and has been deposited with the International Patent Organism Depositary (IPOD) as FERM BP-7648.

2) The Enzymologic Properties of γ-CGTase

The present invention is based on the discovery of γ-CGTase by the present inventors; this enzyme was produced by *Bacillus clarkii* strain 7364. The enzymologic properties thereof are as follows (Example 1). γ-CD producing activity was measured by the following method.

A 450 μL quantity of 1.5 percent soluble starch solution/25 mM Gly-NaCl—NaOH buffer solution (pH 10.5) was maintained at 40° C. and 50 μL of a suitably diluted enzyme solution was added to start the reaction. The reaction was stopped by the addition of 500 μL of 0.05 N HCl at 0, 5, 10, 15, 20, and 30 minutes after the start of the reaction. After admixing 5 mM BCG solution (in 20 percent ethanol) to the reaction solution, the mixture was maintained for 20 min at room temperature, 2 mL of 1 M BCG buffer solution (pH 2.4) was added, and absorbance at 630 nm was measured. The γ-CD content in the reaction solution was obtained from a calibration curve prepared in advance from absorbance values. One unit of γ-CGTase cyclic activity is defined as the quantity of enzyme that produces 1 μmol of γ-CD per unit time of period.

a) Optimum pH

In the measurement of the cyclic activity of γ-CGTase by the BCG method, 150 mg of soluble starch was dissolved in 10 mL of buffer solutions of prescribed pH (pH 3–8: ¼×McIlvaine buffer solution (♦ in FIG. 1), pH 8–10.5: 25 mM Gly-NaCl—NaOH buffer solution (■ in FIG. 1), pH 10.5–11.9: 25 mM Na$_2$HPO$_4$—NaOH buffer solution (■ in FIG. 1)) and 450 μL thereof was employed as substrate solution. As a result, the optimal pH of cyclic activity based on the BCG method was 10.0–10.5 (FIG. 1).

b) Optimum Temperature

Figure 2:
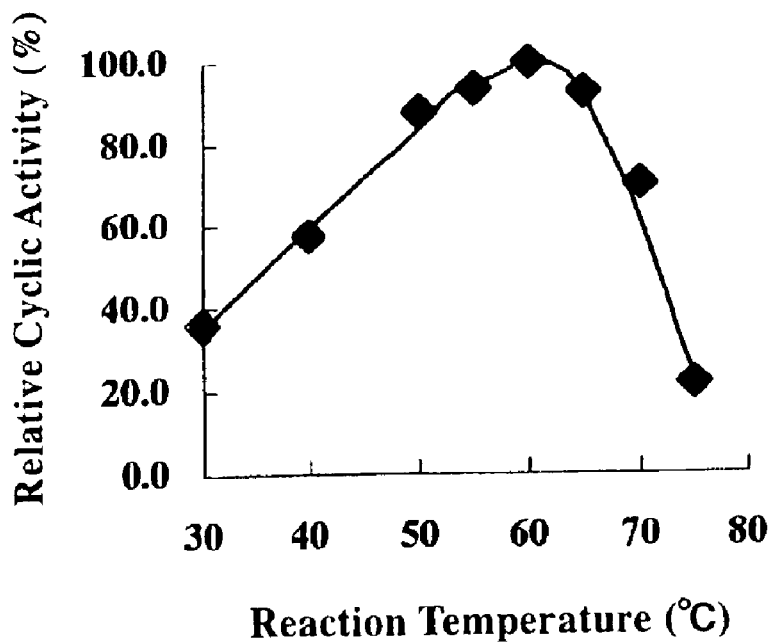
FIG. 2 shows the effects of temperature on γ-CGTase cyclic activity by the BCG method.

In the measurement of the cyclic activity of γ-CGTase by the BCG method, 150 mg of soluble starch was dissolved in 10 mL of 25 mM Gly-NaCl—NaOH buffer solution (pH 10.0) and 450 μL aliquot was employed as substrate solution. The reaction was conducted for 10 min at prescribed temperature. As a result, the optimum temperature for cyclic activity by the BCG method was 60° C. (FIG. 2).

c) pH Stability

Figure 3:
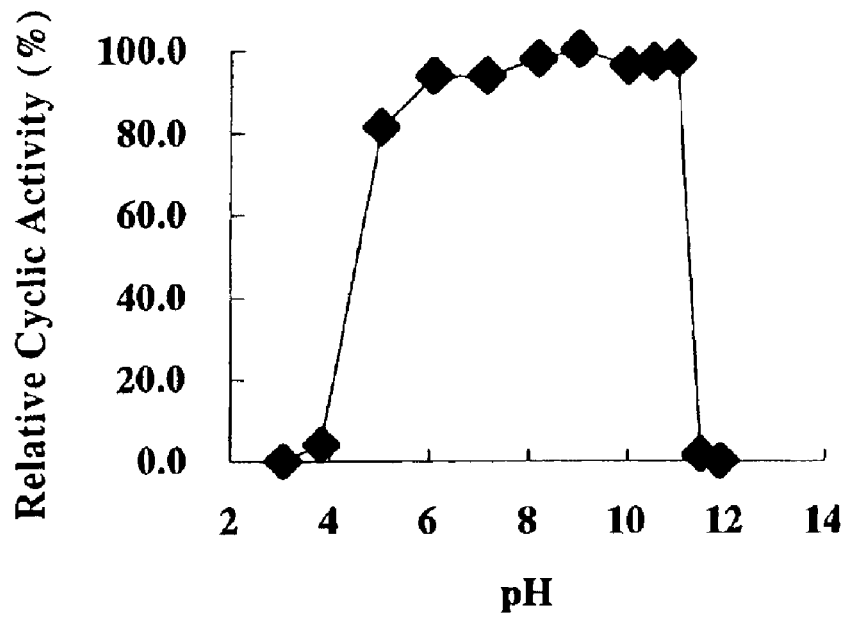
FIG. 3 shows pH stability of γ-CGTase cyclic activity by the BCG method.

In the measurement of the cyclic activity of γ-CGTase by the BCG method, 150 mg of soluble starch was dissolved in 10 mL of 25 mM Gly-NaCl—NaOH buffer solution (pH 10.0) and 450 μL aliquot was employed as substrate solution. A 90 μL quantity of buffer solution of prescribed pH was added to 10 μL of enzyme and each of the pH buffer solutions employed in the measurement of the optimum pH of (a) were employed. After standing for 24 hr at 4° C., 100 mL of 25 mM Gly-NaCl—NaOH buffer solution (pH 10.0) was added and 50 μL aliquot was added to the substrate to start a reaction. The reaction was conducted for 20 min at 40° C. pH stability was achieved from pH 6 to 11 (FIG. 3).

d) Temperature Stability

Figure 4:
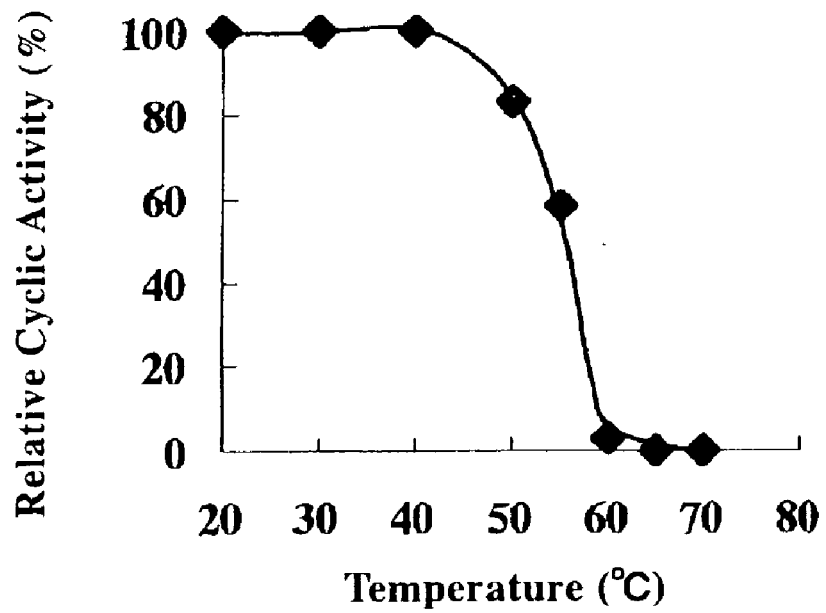
FIG. 4 shows temperature stability of γ-CGTase cyclic activity by the BCG method.

In the measurement of the cyclic activity of γ-CGTase by the BCG method, 150 mg of soluble starch was dissolved in 10 mL of 25 mM Gly-NaCl—NaOH buffer solution (pH 10.0) and 450 μL thereof was employed as substrate solution. A 90 μL quantity of 25 mM Gly-NaCl—NaOH buffer solution (pH 10.0) was added to 10 μL of enzyme and maintained at a prescribed temperature for 15 min, after which 50 μL thereof was added to the substrate to start the reaction. The reaction was conducted at 40° C. for 10 min. After being processed for 15 min at 50° C., the enzyme exhibited more than 80 percent activity of untreated enzyme (FIG. 4).

e) Molecular Weight

The molecular weight of the enzyme by SDS-PAGE calculated from the relative degree of displacement from various standard proteins was 68 KDa.

f) Isoelectric Point

The isoelectric point based on isoelectric point electrophoresis and calculated from the relative degree of displacement from various standard proteins was 3.98.

g) N-Terminal Amino Acid Sequence

Analysis by the usual method with a Gas-Phase Protein Sequencer "Model 477A" from Applied Biosystems revealed the amino acid sequence indicated by SEQ ID No. 3 on the N terminal of the enzyme.

h) Internal Amino Acid Sequence

The enzyme was fragmented by the usual method and the N-terminal sequence of peptide fragments isolated by HPLC was analyzed with a Gas-Phase Protein Sequencer "Model 477A" from Applied Biosystems, revealing the presence of the amino acid sequence indicated by SEQ ID No. 4.

3) γ-CGTase Gene Analysis

A PCR reaction was conducted using primers designed from the internal amino acid sequence and the N-terminal amino acid sequence of mature enzyme using the chromosomal DNA of *Bacillus clarkii* 7364 as template. The PCR fragment obtained was determined to be a gene fragment 1470 bp in length encoding the area beyond the ninth N from the N terminal of γ-CGTase. Next, the chromosomal DNA was completely decomposed with the restriction enzyme Sac I and subjected to self-ligation to obtain cyclic DNA as template. Using antisense primer designed from the upstream sequence of the 1470 bp PCR fragment and sense primer designed from the downstream sequence thereof, inverse PCR was conducted and the entire nucleotide sequence of the targeted enzyme gene was determined.

4) Isolation and Identification of Recombinant γ-CGTase Gene

To confirm that the cloned DNA fragment was the gene encoding the targeted γ-CGTase gene, full F-primer 5'-gACTTgTACTAAgACAACCTTACg-3' and full R-primer 5'-gCATCggCTCTACTCATTTCA-3' were employed and PCR was conducted with chromosomal DNA as template, yielding a 2530 bp PCR fragment comprising the structural gene of γ-CGTase, a promoter, and a transcription termination signal. Next, the DNA fragment was ligated to pGEM-T and inserted into *E. coli* JM-109. The transformed *E. coli* (pGFT-01/JM109) was cultured for 16 hr in LB medium, the bacterial mass was pulverized, and centrifugal separation was employed to remove insoluble matter. The supernatant was confirmed to comprise 0.35 U/mL of activity by means of γ-CD cyclic activity. Further, employing the supernatant as crude enzyme, when it was applied to 1 percent soluble starch (25 mM glycine-NaCl—NaOH buffer solution, pH 10), the enzyme was confirmed by HPLC to be CGTase mainly producing γ-CD.

Next, the pGFT-01/JM109 was cultured on a large scale (600 mL) in LB medium and the γ-CGTase was purified. The purification was conducted in the two stages of a γ-CD bond affinity column and gel filtration, and was conducted to a single band by SDS-PAGE.

Table 2 shows the various properties of the enzyme produced by the transformed *E. coli* (pGFT-01/JM109).

TABLE 2

A comparison of the properties of γ-CGTase produced by *B. clarkii* and *E. coli*

|  | *B. clarkii* | *E. coli* |
|---|---|---|
| Optimum pH | 10.5–11.0 | 10.5–11.0 |
| Optimum temperature | 60° C. | 60° C. |
| Stability (pH) | 6.0–11.0 | 6.0–11.0 |
| Stability (temperature) | 30° C. | 30° C. |
| Molecular weight (SDS-PAGE) | 68,000 | 68,000 |
| Main product | γ | γ |

Activity was measured by the DCG method.

Analysis of the N-terminal of the γ-CGTase produced by the transformed *E. coli* by the usual method using a Gas-Phase Protein Sequencer "Model 477A" from Applied Biosystems revealed that the enzyme had the amino acid sequence shown in SEQ ID No. 3 at the N terminal.

The enzymologic characteristics of the recombinant γ-CGTase matched nearly exactly those of γ-CGTase derived from *Bacillus clarkii* 7364. Accordingly, the DNA encoding the above-described recombinant γ-CGTase was determined to have been derived from *Bacillus clarkii* 7364.

5) Expression/Manufacturing of Gene Encoding Recombinant γ-CGTase a) Expression Vector The γ-CGTase according to the present invention can be produced in the host cell if the host cell is transformed with a DNA molecule comprising the fragment encoding γ-CGTase according to the present invention either in a duplicable state within the host cell or in a state in which the γ-CGTase gene has been incorporated into the chromosomes and is expressable, particularly in the form of an expression vector. Accordingly, based on the present invention, a DNA molecule comprising a gene encoding the γ-CGTase of the present invention, particularly an expression vector, is provided. This vector is preferably a plasmid.

The vector employed in the present invention can be suitably selected from among viruses, plasmids, and cosmid vectors in view of the host cell being employed. For example, when the host cell is *Bacillus subtilis*, a pUB plasmid can be employed. When *E. coli*, a λ-phage bacteriophage, pBR322, BluesscriptIISK(+), pUC18, pUC19, pUC118, pUC119, pGEM-T pCR2.1, pLEX, pJL3, pSW1, pSE280, pSE420, pHY300PLK, and other plasmid vectors can be employed. When expressed by *E. coli*, pBR322, BluesscriptIISK(+), pGEM-T, pUC18, pUC19, pUC118, pUC119, and pCR2.1 are suitable. When expressed by *Bacillus subtilis*, pHY300PLK is suitable. Further examples are pBR and pUC plasmids; for yeast, examples are Yep, Ycp, and YIP vectors. The plasmid preferably comprises a selective marker such as drug resistance of the transformant or a nutritional requirement marker. Further, the expression vector also desirably comprises DNA sequences such as promoters required for expression of γ-CGTase, terminators, ribosome bonding sites, and transcription termination signals.

Promoters normally employed in *E. coli*, such as lac, trp, tac, and T7, are employed with preference. Expression is also possible using promoters employed in the expression of γ-CGTase by wild strains. The sequence from 1 to 702 of the amino acid sequence shown in SEQ ID No. 2 contains a signal peptide; this sequence can be employed as it is as indicated in the examples further below. Promoters such as xylose operon, subutilicin, and SPAC are desirably employed for *Bacillus subtilis,* and promoters such as ADH, PHO, GAL, and GAP are desirably employed for yeast.

b) Transformants/Culturing

Examples of hosts are *E. coli, Bacillus subtilis*, actinomycetes, and yeast; any host that does not produce amylase under the culture conditions of the transformant will suffice. The method of manufacturing CGTase of the present invention is characterized in that the above-described transformed cell is cultured and in that a protein having cyclodextrin glucanotransferase activity on a substrate selected from among starch and its decomposition products and producing γ-cyclodextrin as a main product is collected from the cultured product. Further, the recombinant γ-CGTase of the present invention is an expression product of the above-described gene. That is, the γ-CGTase of the present invention is a protein having essentially the same amino acid sequence (the amino acid sequence itself or that amino acid sequence into which one or multiple amino acid sequences have been substituted, inserted, added or deleted) as the amino acid sequence denoted by amino acid residues 1 to 702 in SEQ ID No. 2 or the amino acid sequence denoted by amino acid residues 29 to 702 in SEQ ID No. 2, and having cyclodextrin glucanotransferase activity on starch, dextrin, amylopectin or amylose and producing γ-CD as a main product (that is, producing γ-CD as a main product, with the quantity of β- and α-cyclodextrin produced being lower than the quantity of γ-cyclodextrin produced).

The nutritive medium employed to culture the transformant of the present invention can be a natural medium or a synthetic medium so long as it comprises a carbon source, nitrogen source, inorganic matter, and, as needed, trace nutritive elements required by the bacterial strain employed. Examples of carbon sources are glucose, maltose, and other maltooligosaccharides, fructose, starch, dextrin, glycerin, and other hydrocarbons. Examples of nitrogen sources are ammonium chloride, ammonium sulfate, ammonium nitrate, sodium nitrate, glutamic acid, other amino acids, urea, and other inorganic nitrogen and organic nitrogen compounds. Further examples are peptones, polypeptones, meat extracts, yeast extracts, CSL, soybean powder, soybean meal, dried yeast, casamino acids, and other nitrogen-comprising organic natural products. Examples of inorganic compounds suitable for use are potassium dihydrogenphosphate, dipotassium hydrogenphosphate, magnesium sulfate, ferrous sulfate, manganese sulfate, zinc sulfate, sodium chloride, potassium chloride, and calcium chloride. Additionally, trace nutrients such as biotin and thiamin may also be employed as needed. A liquid culture method may be employed as the culture method; industrially, a ventilated stirring culture method is suitable. The culture temperature and pH may be suitably selected for proliferation of the transformant being employed. Although the culture period varies, when the production of recombinant γ-CGTase has been confirmed, the culture is desirably stopped when the production quantity has reached a maximum. To collect the recombinant γ-CGTase of the present invention from the cultured product obtained in this manner, the bacterial mass in the culture solution is first broken down by a physical means such as supersonic, or the cell membrane is dissolved with an organic solvent or an enzyme such as lysozyme, after which the residue is removed by centrifugal separation or filtration. The product is then subjected to membrane ultrafiltration, salting out, solvent precipitation, or the like to prepare a concentrated crude enzyme solution for industrial application. A purified enzyme preparation of the concentrated enzyme can be readily obtained by a combination of widely known isolation and purification methods, such as affinity chromatography in which the γ-CD is fixed, ion-exchange chromatography, and gel filtration chromatography.

c) Method of Manufacturing CD-Comprising Compositions Having γ-CD and a Desired CD Balance (α-, β-, and γ-CD Balance)

The present invention provides methods of manufacturing CD-comprising compositions having γ-CD and a desired CD balance (α-, β-, and γ-CD balance) using the above-described γ-CGTase. That is, to manufacture CD by means of the present invention, for example, 0.1–300 U (per gram of dry starch) of the recombinant γ-CGTase enzyme solution (purified enzyme or crude enzyme) alone or in combination with CGTase (α- and β-CGTase) produced by a microbe of some other origin is added to an aqueous solution comprising 1–30 percent starch (including starch, compositional fractions thereof, or processed starches) and an enzymatic reaction is conducted for 1–96 hours at a temperature of from 20–60° C. and a pH of from 4.5–12. As needed, the starch can be preheated or liquefied for use.

The sugar (containing composition) prepared by the above-described method sometimes contains monosaccharides such as glucose, various oligosaccharides (such as maltose), or dextrin and the like in addition to α-, β-, and γ-CD and the like. Further, as needed, CD of a single desired degree of polymerization can be separated (by crystallization, chromatographic fractionation, fermentation treatment with yeast or the like, or enzymatic processing) for use. The form employed, in addition to incorporation into a composition prepared in the method set forth above, can be crystalline, a freeze-dried product, a powder, grains, or any other form. The CD of the present invention can be added to or present in all food products that can be orally consumed in the same manner as CDs that have been commercially sold to date, such as tea, beverages such as cold drinks, candy, jelly, Japanese finger foods, Japanese and Western snacks, yogurt, ice-cream, and other dairy products, ham, sausage, and other processed meat products, boiled fish paste, naruto, and other processed seafood products, noodles, pickled vegetables, and other seasoned processed foods, and instant foods, in order to stabilize fragrance materials, emulsify, or serve as excipients. The use of safe food additives in the form of CDs permits extremely convenient and effective improvement in the desirability and functionality of food products. In addition to use in food products, CDs can also be used to stabilize active ingredients, emulsify, and serve as excipients in pharmaceuticals and cosmetics.

The method of employing the CD of the present invention is not specifically limited other than that the CD be present in food, pharmaceuticals, or cosmetics. For example, CD can be simultaneously added to food and drink materials as a base during processing, or added after completion of processing of the base food or drink product; any method of addition suited to the actual manufacturing steps of various food products can be employed. The quantity of CD added is not particularly limited so long as the flavor or aroma of the base food or drink is not lost. Generally, the addition of an amount not exceeding 20 weight percent is desirable. At greater than 20 weight percent, the masking effect of the CD changes the flavor or aroma of the base food or drink product, potentially reducing the desirability of the product. In pharmaceuticals and cosmetics, there is no specific limit so long as the efficacy of active ingredients is not compromised.

EXAMPLES

Examples of the present invention are given below by way of describing the present invention more specifically; the present invention is not limited to the scope of the Examples given below.

Enzyme produced by *Bacillus clarkii* was prepared by the following method.

*Bacillus clarkii* strain 7364 (FERM BP-7156) was cultured with vibrating for 48 hr at 37° C. in a liquid medium comprising a carbon source in the form of 1.0 percent (w/v) of Neotack #30T (from Nihon Shokuhin Kakō (K.K.)), a nitrogen source in the form of 0.5 percent of Soya Flour FT (from Nissei Seiyu), 0.5 percent yeast extract (from Difco), 0.1 percent of $K_2HPO_4$, 0.02 percent of $MgSO_4 \cdot 7H_2O$, and 0.8 percent of $Na_2CO_3$. CGTase was secreted into the culture solution (Blue value method 20 U/mL culture supernatant).

The CGTase obtained was purified by affinity chromatography.

γ-CGTase activity was measured by the following method as γ-CD production activity (cyclization activity).

A 450 μL quantity of 1.5 percent soluble starch solution/ 25 mM Gly-NaCl—NaOH buffer solution (pH 10.5) was maintained at 40° C. and 50 μL of suitably diluted enzyme solution was added to start the reaction. At 0, 5, 10, 15, 20, and 30 min after the start of the reaction, 500 μL of 0.05 N HCl was added to stop the reaction. 5 mM BCG solution (in 20 percent ethanol) was admixed, the mixture was maintained for 20 min at room temperature, 2 mL of 1 M BCG buffer solution (pH 4.2) was added, and absorbance was measured at 630 nm. The γ-CD content in the reaction solution was obtained from a calibration curve prepared in advance from absorbance values. One unit of γ-CGTase cyclic activity was defined as the quantity of enzyme producing 1 μmol of γ-CD per unit time under the above-stated reaction conditions.

Example 1

Enzymologic Characteristics of Purified γ-CGTase

Example 1-1

Preparation of Purified Enzyme

*Bacillus clarkii* strain 7364 was cultured and the γ-CGTase produced by this bacterial strain was purified by affinity chromatography.

Example 1–2

Enzymologic Characteristics of Purified Enzyme

1) Action

A substrate solution was prepared by dissolving a substrate in the form of soluble starch to 10 percent (w/v) in 50 mM glycine-NaCl—NaOH (pH 10.0) buffer solution. A 0.5 U/g DS quantity of the above-described purified enzyme was added to 5 mL of the substrate solution and reacted for 48 hr at 50° C. When the reaction product was checked by the HPLC method described in Japanese Patent Application Un-examined Publication No. 2001-327299, 9.7 percent γ-CD, 1.7 percent α-CD, and 0.9 percent β-CD (HPLC area) had been produced after 48 hr.

2) Optimum pH

The cyclic activity of γ-CGTase was measured by the BCG method by dissolving 150 mg of soluble starch in 10 mL of buffer solutions of prescribed pH (pH 3–8: ¼×McIlvaine buffer solution, pH 8–10.5: 25 mM Gly-NaCl—NaOH buffer solution; pH 10.5–11.9: 25 mM Na$_2$HPO$_4$—NaOH buffer solution) and employing 450 μL thereof as substrate solution. As a result, the optimum pH for cyclic activity based on the BCG method was pH 10.0–10.5 (FIG. 1).

3) Optimum Temperature

In the measurement of the cyclic activity of γ-CGTase by the BCG method, 150 mg of soluble starch was dissolved in 10 mL of 25 mM Gly-NaCl—NaOH buffer solution (pH 10.0) and 450 μL thereof was employed as substrate solution. The reaction was conducted for 10 min at prescribed temperature. As a result, the optimum temperature for cyclic activity by the BCG method was 60° C. (FIG. 2).

4) pH Stability

In the measurement of the cyclic activity of γ-CGTase by the BCG method, 150 mg of soluble starch was dissolved in 10 mL of 25 mM Gly-NaCl—NaOH buffer solution (pH 10.0) and 450 μL thereof was employed as substrate solution. A 90 μL quantity of buffer solution of prescribed pH was added to 10 μL of enzyme and each of the pH buffer solutions employed in the measurement of the optimum pH of (2) were employed. After standing for 24 hr at 4° C., 100 mL of 25 mM Gly-NaCl—NaOH buffer solution (pH 10.0) was added and 50 μL thereof was added to the substrate to start the reaction. The reaction was conducted for 20 min at 40° C. pH stability was achieved from pH 6 to 11 (FIG. 3).

5) Temperature Stability

In the measurement of the cyclic activity of γ-CGTase by the BCG method, 150 mg of soluble starch was dissolved in 10 mL of 25 mM Gly-NaCl—NaOH buffer solution (pH 10.0) and 450 μL thereof was employed as substrate solution. A 90 μL quantity of 25 mM Gly-NaCl—NaOH buffer solution (pH 10.0) was added to 10 μL of enzyme and maintained at a prescribed temperature for 15 min, after which 50 μL thereof was added to the substrate to start the reaction. The reaction was conducted at 40° C. for 10 min. After being processed for 15 min at 50° C., the enzyme exhibited more than 80 percent activity of untreated one (FIG. 4).

6) Molecular Weight

The molecular weight of the enzyme by SDS-PAGE calculated from the relative degree of displacement from various standard proteins was 68 KDa.

7) Isoelectric Point

The isoelectric point based on isoelectric point electrophoresis and calculated from the relative degree of displacement from various standard proteins was 3.98.

8) N-Terminal Amino Acid Sequence

Analysis by the usual method with a Gas-Phase Protein Sequencer "Model 477A" from Applied Biosystems revealed that the enzyme had the amino acid sequence indicated by SEQ ID No. 3 on the N terminal.

9) Internal Amino Acid Sequence

The enzyme was fragmented by the usual method and the N-terminal sequence of peptide fragments isolated by HPLC were analyzed with a Gas-Phase Protein Sequencer "Model 477A" from Applied Biosystems, revealing the presence of the amino acid sequence indicated by SEQ ID No. 4.

Example 2

Example 2–1

Preparation of Chromosomal DNA

The chromosomal DNA of *Bacillus clarkii* 7364 was prepared with reference to the report of N. Declerck et al. (N. Declerck, P. Joyet, D. Le Coq and H. Heslot, J. Biotech., 8, 1998, 23–38). *Bacillus clarkii* strain 7364 was cultivated in enzyme-producing medium and the bacterial mass was centrifugally separated (8,000 rpm, 10 min) from the culture solution (40 mL). The bacterial mass obtained was washed twice with 5 mL of TESS buffer solution (30 mM Tris/HCl (pH 7.5), 5 mM EDTA, 50 mM NaCl, 25 percent sucrose) and suspended in 3 mL of the same buffer solution. The bacterial mass suspension was processed for 10 min at 65° C. and cooled to 37° C. A 1 mL quantity of lisozyme aqueous solution (50 mg/mL) was added and the mixture reacted for 1 hr at 37° C. Next, proteinase K was dissolved in water to 25 mg/mL, self-digested for 1 hr at 37° C., 500 μL of the solution was added, and the mixture was reacted for 2 hr at the same temperature. The reaction was then stopped by adding 1 mL quantity of 10 percent SDS and processing for 10 min at 65° C. The reaction solution was processed (twice) with TE saturated phenol and phenol/chloroform and precipitated from ethanol to recover chromosomal DNA, which was dissolved in 1.2 mL of TE. RNAase solution (500 μg/mL) was added to 10 μg/mL and the mixture was reacted for 2 hr at 37° C. The product was processed with phenol/chloroform (twice) and precipitated from ethanol to recover chromosomal DNA. This operation yielded 162 μg of chromosomal DNA.

Example 2–2

Obtaining and Determining the Nucleotide Sequence of DNA Fragments Encoding γ-CGTase Plasmid preparation, restriction digestion, ligation, and transformation of *E. coli* were conducted based on reported methods (Sambrook, J., Fritsch, E. F. & Maniatis, T. (1982) Molecular cloning: a laboratory manual, $2^{nd}$ edn, Cold Spring Harbor Laboratory, Cold Spring Harbor, N.Y.). The nucleotide sequence was determined by the dideoxy chain termination method using a multicapillary CNA analysis system CEQ2000 from Beckman Coulter. A GENETYX-WIN was employed for nucleotide sequence determination and computer analysis of DNA strands.

The partial gene fragment encoding γ-CGTase was prepared by PCR using chromosomal DNA as template and the N-terminal F primer: 5'-AAYgTIAAITAYgCIgARgARgT-3' (SEQ ID NO: 5) and the domain Cr primer: 5'-gCRTCICCIggYTTICCCATDCC-3' (SEQ ID NO: 6). The N-terminal F primer was designed as the N-V-N-Y-A-E-E (residues 9–15 of SEQ ID NO: 3) following number 9 in the N-terminal amino acid sequence of mature protein determined by the Edman method, and the domain Cr primer was designed based on the PMGKPGDA (residues 13–20 of SEQ ID NO: 4) portion of the N-terminal amino acid sequence of a peptide fragment obtained by random decomposition of the protease of mature protein. The PCR reaction conditions are given below.

TABLE 3

| | |
|---|---|
| Chromosomal DNA | 2 μl (360 ng) |
| N-terminal F primer (200 pmol/μl) | 0.25 μl |
| Domain Cr primer (200 pmol/μl) | 0.25 μl |
| 10 × PCR buffer | 5 μl |
| dNTP | 4 μl |
| 25 mM MgCl₂ | 4 μl |
| dH₂O | 33.25 μl |
| Taq polymerase | 0.25 μl |

Takara Ex Taq ™ was employed.

The reaction solution was heated to 94° C. for 5 min; a cycle of heating the reaction solution to 94° C. for 1 min, 51° C. for 2 min, and 72° C. for 3 min was repeated 30 times; and the reaction solution was finally maintained at 72° C. for 10 min. The roughly 1,500 bp fragment obtained by PCR was ligated to T-vector pGEM-T and the nucleotide sequence was determined. Sequences precisely matching the N-terminal amino acid sequences obtained by Edman analysis (mature enzyme N-terminal amino acid sequence and peptide N-terminal sequence in the enzyme portion) were found in the amino acid sequence inferred from the nucleotide sequencing. The consensus sequence of an amylase family enzyme group was also discovered. Accordingly, this gene fragment was determined to be the 1470 bp fragment encoding the area beyond number 9 from the N-terminal of the mature γ-CGTase enzyme protein.

The chromosomal DNA prepared in the above-described Example was fully digested with the restriction enzymes SacI, EcoRI, BamHI, and the like and isolated by agarose gel electrophoresis. The isolated DNA fragments were transferred to nylon film by the usual method. In the PCR conducted in the course of obtaining the above-described 1470 bp fragment, dNTP that had been Dig labeled in a 1:1 ratio with dNTP was admixed, and PCR was conducted under the same conditions to prepare Dig-labeled 1470 bp DNA fragments. These were Southern hybridized with the DNA fragments that had been fixed to the above-described nylon film (Southern et al., J. Mol. Biol., 98, 503–517, 1975). Hybridization was conducted for 16–20 hr at 65° C. in a solution comprising 0.5 mg/mL of denature salmon DNA, 10 percent dextran, 1 percent SDS, and 5×SSC. The product was washed three times for 30 min at 65° C. in a solution comprising 1 percent SDS and 2×SSC. As a result, roughly 2,500 bp fragments of DNA fragments digested with SacI were hybridized.

Next, the following test was conducted to obtain the 5'- and 3'-upstream and downstream regions of the fragment. First, chromosomal DNA was fully digested with SacI. T4DNA ligase was then added under suitable conditions to make the digested product form monomeric circles and the mixture was reacted for a day and a night at 16° C. (digested chromosomal DNA 1 μg, 10×ligation buffer 10 μL, T4 ligase 700 U/1 mL). PCR was then conducted using the SacI-self-circulized DNA molecules as templates, the inverse anti primer: 5'-gATCTgTTACAATATgATAAAT-3' (SEQ ID NO: 7), and the inverse sense primer: 5'-TTATTAGACggTCAATCGTTA-3' (SEQ ID NO: 8). The inverse anti primer was designed from the 5'-upstream region of the above-described 1470 bp fragment and the inverse sense primer was designed based on the 3'-downstream nucleotide sequence of the above-described 1470 bp fragment. The PCR reaction conditions are given below.

TABLE 4

| | |
|---|---|
| Sac I-self-circulized DNA | 6 μl (240 ng) |
| inverse anti primer (200 pmol/μl) | 0.25 μl |
| inverse sense primer (200 pmol/μl) | 0.25 μl |
| 10 × PCR buffer | 5 μl |
| dNTP | 4 μl |
| 25 mM MgCl₂ | 4 μl |
| dH₂O | 30.25 μl |
| Taq polymerase | 0.25 μl |

Takara Ex Taq ™ was employed.

The reaction solution was heated to 94° C. for 5 min; a cycle of heating the reaction solution to 94° C. for 0.5 min, 47° C. for 0.5 min, and 72° C. for 0.5 min was repeated 10 times; a cycle of heating the reaction solution to 94° C. for 0.5 min, 50° C. for 0.5 min, and 72° C. for 1 min was repeated 10 times; a cycle of heating the reaction solution to 94° C. for 1 min, 50° C. for 2 min, and 72° C. for 3 min was repeated 10 times; and the reaction solution was finally maintained at 72° C. for 10 min. The roughly 2,000 bp fragment obtained by PCR was ligated to T-vector pGEM-T, and the nucleotide sequence was determined. As a result, the upstream region nucleotide sequence of about 0.4 Kbp comprising the initiation codon and the remaining N-terminal sequence of the γ-CGTase, the ribosome bond area (RBS), and the promoter sequence; and the downstream region nucleotide sequence of about 0.2 Kbp comprising the remainder of the C terminal region, termination codon, and inverted repeat were determined. The nucleotide sequence shown in SEQ ID No. 1 was determined.

Example 2–3

Recombinant Plasmid pGFT-01 and Transformation of *E. Coli*

PCR of the γ-CGTase gene shown in SEQ ID No. 1 and its flanking region was conducted using chromosomal DNA as template, the full F-primer: 5'-gACTTgTACTAAgACAACCTTACg-3' (SEQ ID NO: 9), and the full R-primer: 5'-gCATCggCTCTACTCATTTCA-3' (SEQ ID NO: 10) as primers. The primers employed in the reaction were designed from the 237 bp upstream sequence from the initiation codon and the 77 bp downstream nucleotide sequence from the termination codon.

The PCR reaction conditions are given in the table below.

TABLE 5

| | |
|---|---|
| Chromosomal DNA | 2 μl (360 ng) |
| Full F-primer (200 pmol/μl) | 0.25 μl |
| Full R-primer (200 pmol/μl) | 0.25 μl |
| 10 × PCR buffer | 5 μl |
| dNTP | 4 μl |
| 25 mM MgCl₂ | 4 μl |
| dH₂O | 33.25 μl |
| Taq polymerase | 0.25 μl |

Takara Ex Taq ™ was employed.

The above-described reaction solution was heated to 94° C. for 5 min; a cycle of heating the reaction solution to 94° C. for 1.0 min, 55° C. for 1.5 min, and 72° C. for 3 min was repeated 32 times; and the reaction solution was finally maintained at a temperature of 72° C. The roughly 2.5 Kbp DNA fragment obtained was ligated to T-vector pGEM-T and inserted into *E. coli* JM109, and plasmid pGFT-01 was prepared in large quantity. Primer walking was then employed to confirm the entire nucleotide sequence. It was confirmed that DNA comprising at least the nucleotide sequence shown in SEQ ID No. 1 was contained.

Example 3

Purification and Enzymologic Properties of γ-CGTase Produced by E. Coli pGFT-01/JM109 was cultured in large quantity (600 mL) in LB medium and the γ-CGTase was purified. In accordance with the method of Example 1, purification was conducted in the two-stage process of a γ-CD bond affinity column and gel filtration, followed by purification to a single band by SDS-PAGE. A 15.5 mg (79.8 U) quantity of protein was obtained (recovery rate 73 percent).

Table 6 shows the properties of the enzyme produced by the transformed E. coli (pGFT-01/JM109).

TABLE 6

Comparison of Various Properties of γ-CGTase Produced by B. clarkii and E. coli

|  | B. clarkii | E. coli |
|---|---|---|
| Optimum pH | 10.5–11.0 | 10.5–11.0 |
| Optimum Temperature | 60° C. | 60° C. |
| Stability (pH) | 6.0–11.0 | 6.0–11.0 |
| Stability (Temp.) | 30° C. | 30° C. |
| Molecular Weight (SDS-PAGE) | 68,000 | 68,000 |
| Main Product | γ | γ |

Figure 5:
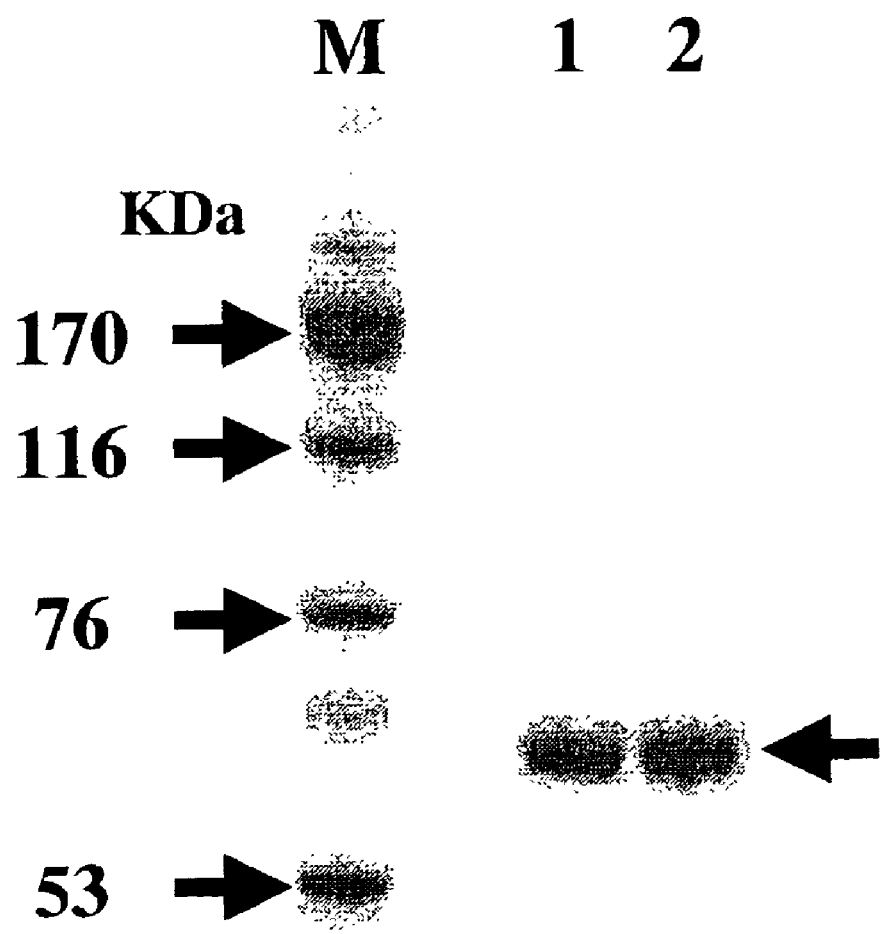
FIG. 5 shows the results of SDS-PAGE on the enzyme (1) produced by *B. clarkii* and the enzyme (2) produced by *E. coli*.

The activity of both enzymes was measured by the BCG method. The conditions employed in activity measurement were identical to those set forth above. FIG. 5 shows the results of SDS-PAGE on the enzyme (1) produced by B. clarkii and the enzyme (2) produced by E. coli. The enzyme produced by E. coli exhibited properties nearly identical to those of the enzyme produced by B. clarkii.

Example 4

Preparation of CD-Comprising Composition Using γ-CGTase Produced by E. Coli (1)

Cornstarch was liquefied with α-amylase by the usual method and a liquid starch solution with a concentration of 20 weight percent and a glucose equivalent of 7 was prepared. The liquid starch solution was adjusted to pH 7 and the γ-CGTase produced by E. coli described in Example 3 was concentrated using a UF concentration film (PM-10) as a crude enzyme solution. One unit/g of substrate of this enzyme solution was added and the reaction was conducted at 55° C. for 48 hr. Subsequently, the reaction solution was heated to deactivate the enzyme and purification such as decoloring and ion-exchange was conducted to prepare a CD-comprising composition. The sugar composition thereof was determined by HPLC.

TABLE 7

| α-CD | 1.7% |
|---|---|
| β-CD | 0.8% |
| γ-CD | 8.2% |
| Other sugars | 89.3% |

Example 5

Preparation of CD-Comprising Composition Using γ-CGTase Produced by E. Coli (2)

Cornstarch was liquefied with α-amylase by the usual method and a liquid starch solution with a concentration of 10 weight percent and a glucose equivalent of 7 was prepared. The liquid starch solution was adjusted to pH 7. The γ-CGTase produced by E. coli described in Example 3 was concentrated using a UF concentration film (PM-10) as a crude enzyme solution, two units/gram of substrate were added, and a reaction was conducted at 55° C. for 48 hr. Subsequently, the temperature of the reaction solution was raised to 90° C. to deactivate the enzyme, the reaction solution was cooled to 75° C., 40 units per gram of substrate of Bacillus-derived CGTase (from Nihon Shokuhin Kakō) was added, and the reaction was conducted for 24 hr. The reaction solution was heated to 90° C. to deactivate the enzyme and purification such as decoloring and ion-exchange was conducted to prepare a CD-comprising composition. The sugar composition thereof was determined by HPLC.

TABLE 8

| α-CD | 9.8% |
|---|---|
| β-CD | 7.2% |
| γ-CD | 6.2% |
| Other sugars | 76.8% |

Example 6

Cornstarch was liquefied with α-amylase by the usual method and a liquid starch solution with a concentration of 10 weight percent and a glucose equivalent of 7 was prepared. The liquid starch solution was adjusted to pH 7. The γ-CGTase produced by E. coli described in Example 3 was concentrated using UF concentration film (PM-10) as a crude enzyme solution. Three units of this enzyme solution and 20 units of CGTase derived from Bacillus (from Nihon Shokuhin Kakō (K.K.) per gram of substrate were simultaneously added and the reaction was conducted at 55° C. for 72 hr. Subsequently, the reaction solution was heated to 90° C. to deactivate the enzyme and purification such as decoloring and ion-exchange was conducted to prepare a CD-comprising composition. The sugar composition thereof was determined by HPLC.

TABLE 9

| α-CD | 7.8% |
|---|---|
| β-CD | 4.0% |
| γ-CD | 5.8% |
| Other sugars | 82.4% |

Based on alkalophilicc Bacillus bacteria discovered by the present inventors, particularly based on a γ-CGTase gene derived from B. clarkii, the present invention produces recombinant γ-CGTase-producing microbes which are cultivated by genetic engineering methods to improve enzyme production properties and produce γ-CGTase with few impurities; the present invention is thus quite useful. Further, the present invention is extremely valuable because, since it is possible to produce the recombinant enzyme on an industrial scale, CD-comprising compositions having γ-CD and a desired CD balance (α-, β-, and γ-CD balance) can be manufactured with great efficiency.

The present disclosure relates to the subject matter contained in Japanese Patent Application No. 2001-211340 filed on Jul. 11, 2001, which is expressly incorporated herein by reference in its entirety.

What is claimed is:

1. An isolated protein having the amino acid sequence of amino acid residues 1 to 702 denoted by SEQ ID NO: 2 in the Sequence Listing.

2. An isolated protein having the amino acid sequence of amino acid residues 29 to 702 denoted by SEQ ID NO: 2 in the Sequence Listing.

3. An isolated protein encoded by a nucleotide sequence hybridizing under stringent conditions with a nucleic acid molecule having a complementary nucleotide sequence to the isolated nucleic acid molecule encoding a protein having the amino acid sequence of amino acid residues 1 to 702 denoted by SEQ ID NO: 2 in the attached Sequence Listing.

4. An isolated protein encoded by a nucleotide sequence hybridizing under stringent conditions with a nucleic acid molecule having a complementary nucleotide sequence to the isolated nucleic acid molecule encoding a protein having the amino acid sequence of amino acid residues 29 to 702 denoted by SEQ ID NO: 2 in the attached Sequence Listing.

5. An isolated protein encoded by a nucleotide sequence hybridizing under stringent conditions with an isolated nucleic acid molecule having the nucleotide sequence of nucleotides 321 to 2,426 or the nucleotide sequence of nucleotides 405 to 2,426 of SEQ ID NO: 1 of the attached Sequence Listing.

* * * * *

SEQUENCE LISTING

<160> NUMBER OF SEQ ID NOS: 10

<210> SEQ ID NO 1
<211> LENGTH: 2530
<212> TYPE: DNA
<213> ORGANISM: Bacillus clarkii
<220> FEATURE:
<223> OTHER INFORMATION: 7364
<220> FEATURE:
<221> NAME/KEY: CDS
<222> LOCATION: (321)..(2426)

<400> SEQUENCE: 1

```
gacttgtact aagacaacct tacgaaccct tttagatttt gttccaaaag gcaatgattt        60
cgcgcgatgc gcccaactcc aaggcgccta ttctctcaat gtgcatctgg taaacgttgt       120
atccattgta attgtaaaaa aaccgtggaa aatattgact ttgacagtgt aatgttatac       180
aatggatagt gcaaacgatt gcgcaaaaaa tgtagtctgt ttgcactgcg agtaagaagg       240
gagggatatc gttttccagg ttgctttcaa acaccaggat cttcatctat tgataaaaaa       300
cattatgagg aggatttaac gtg ttt cga aaa tta ctc tgt acg tta gtg acg       353
              Val Phe Arg Lys Leu Leu Cys Thr Leu Val Thr
                1               5                  10 atc att aca ttg agt gca tgg att gtt agc cat ggc gga gaa gta cac         401
Ile Ile Thr Leu Ser Ala Trp Ile Val Ser His Gly Gly Glu Val His
             15                  20                  25 gca agt aat gca acg aac gat ttg tcg aat gtc aat tat gcg gag gaa         449
Ala Ser Asn Ala Thr Asn Asp Leu Ser Asn Val Asn Tyr Ala Glu Glu
         30                  35                  40 gtc att tat cac att gta aca gat cgg ttt aaa gac gga gat cct gac         497
Val Ile Tyr His Ile Val Thr Asp Arg Phe Lys Asp Gly Asp Pro Asp
     45                  50                  55 aac aat cct caa gga cag ctg ttt agt aat ggt tgc agt gat ctc aca         545
Asn Asn Pro Gln Gly Gln Leu Phe Ser Asn Gly Cys Ser Asp Leu Thr
 60                  65                  70                  75 aag tat tgc ggt ggt gac tgg cag ggc att atc gat gaa att gaa agc         593
Lys Tyr Cys Gly Gly Asp Trp Gln Gly Ile Ile Asp Glu Ile Glu Ser
                 80                  85                  90 ggt tac cta ccg gat atg gga att act gct ctg tgg atc tcc cct cct         641
Gly Tyr Leu Pro Asp Met Gly Ile Thr Ala Leu Trp Ile Ser Pro Pro
             95                 100                 105 gtt gag aat gta ttt gat tta cat cct gaa ggc ttt tcc tct tat cac         689
Val Glu Asn Val Phe Asp Leu His Pro Glu Gly Phe Ser Ser Tyr His
        110                 115                 120 ggg tat tgg gcc cga gac ttt aaa aag aca aac cct ttc ttc gga gat         737
Gly Tyr Trp Ala Arg Asp Phe Lys Lys Thr Asn Pro Phe Phe Gly Asp
    125                 130                 135 ttt gat gat ttt tcc cga cta atc gaa aca gct cat gca cat gac ata         785
Phe Asp Asp Phe Ser Arg Leu Ile Glu Thr Ala His Ala His Asp Ile
140                 145                 150                 155 aaa gta gtt att gat ttt gta cct aac cat act tcc cct gta gac atc         833
Lys Val Val Ile Asp Phe Val Pro Asn His Thr Ser Pro Val Asp Ile
                160                 165                 170 gag gat ggt gca ttg tat gac aac ggt aca tta ctg ggc cac tat tca         881
Glu Asp Gly Ala Leu Tyr Asp Asn Gly Thr Leu Leu Gly His Tyr Ser
            175                 180                 185 acg gat gca aac aat tat ttt tat aac tat ggt ggt tca gac ttc tca         929
Thr Asp Ala Asn Asn Tyr Phe Tyr Asn Tyr Gly Gly Ser Asp Phe Ser
        190                 195                 200
```

```
                                                                        -continued gac tat gaa aat agc atc tat cga aac ttg tat gat tta gca agt ctt           977
Asp Tyr Glu Asn Ser Ile Tyr Arg Asn Leu Tyr Asp Leu Ala Ser Leu
    205                 210                 215 aac cag caa cat tcc ttt att gat aaa tac tta aaa gaa tct att caa          1025
Asn Gln Gln His Ser Phe Ile Asp Lys Tyr Leu Lys Glu Ser Ile Gln
220                 225                 230                 235 tta tgg ttg gat acg gga att gac ggg att cgc gtg gat gcg gtt gca         1073
Leu Trp Leu Asp Thr Gly Ile Asp Gly Ile Arg Val Asp Ala Val Ala
                240                 245                 250 cac atg cct ttg ggc tgg caa aaa gca ttt atc tca tct gtc tat gat         1121
His Met Pro Leu Gly Trp Gln Lys Ala Phe Ile Ser Ser Val Tyr Asp
            255                 260                 265 tac aat cca gtt ttt acc ttt ggt gaa tgg ttt aca gga gca caa ggc         1169
Tyr Asn Pro Val Phe Thr Phe Gly Glu Trp Phe Thr Gly Ala Gln Gly
        270                 275                 280 agc aat cat tac cac cat ttt gtc aac aac agt ggc atg agc gcc ctt         1217
Ser Asn His Tyr His His Phe Val Asn Asn Ser Gly Met Ser Ala Leu
    285                 290                 295 gat ttt cgc tat gct cag gta gcg cag gat gta tta aga aat caa aag         1265
Asp Phe Arg Tyr Ala Gln Val Ala Gln Asp Val Leu Arg Asn Gln Lys
300                 305                 310                 315 gga acg atg cat gac att tac gac atg ttg gca agc act caa tta gat         1313
Gly Thr Met His Asp Ile Tyr Asp Met Leu Ala Ser Thr Gln Leu Asp
                320                 325                 330 tat gag cgg ccg caa gat caa gta acc ttt att gat aat cat gat atc         1361
Tyr Glu Arg Pro Gln Asp Gln Val Thr Phe Ile Asp Asn His Asp Ile
            335                 340                 345 gat cgc ttt acg gtg gaa ggc cga gat aca agg aca acg gac atc gga         1409
Asp Arg Phe Thr Val Glu Gly Arg Asp Thr Arg Thr Thr Asp Ile Gly
        350                 355                 360 ctg gca ttt ctt ttg aca tca aga ggc gta ccg gct att tat tat ggt         1457
Leu Ala Phe Leu Leu Thr Ser Arg Gly Val Pro Ala Ile Tyr Tyr Gly
    365                 370                 375 acg gaa aac tat atg act ggt aaa gga gat cca gga aac aga aaa atg         1505
Thr Glu Asn Tyr Met Thr Gly Lys Gly Asp Pro Gly Asn Arg Lys Met
380                 385                 390                 395 atg gag agc ttt gat caa aca acg aca gcc tat cag gtc atc caa aag         1553
Met Glu Ser Phe Asp Gln Thr Thr Thr Ala Tyr Gln Val Ile Gln Lys
                400                 405                 410 ctg gca ccg ctc cga caa gaa aat aaa gcg gtg gta tat ggt tca aca         1601
Leu Ala Pro Leu Arg Gln Glu Asn Lys Ala Val Val Tyr Gly Ser Thr
            415                 420                 425 aaa gaa cgt tgg att aac gat gat gtg ctc att tat gaa cga tcg ttt         1649
Lys Glu Arg Trp Ile Asn Asp Asp Val Leu Ile Tyr Glu Arg Ser Phe
        430                 435                 440 aat gga gat tat ctt tta gtc gca att aat aaa aat gta aat caa gct         1697
Asn Gly Asp Tyr Leu Leu Val Ala Ile Asn Lys Asn Val Asn Gln Ala
    445                 450                 455 tat act att tcc ggt ttg ctc acg gaa atg ccc gcg caa gtc tat cat         1745
Tyr Thr Ile Ser Gly Leu Leu Thr Glu Met Pro Ala Gln Val Tyr His
460                 465                 470                 475 gat gtt tta gac agc tta tta gac ggt caa tcg tta gca gta aaa gaa         1793
Asp Val Leu Asp Ser Leu Leu Asp Gly Gln Ser Leu Ala Val Lys Glu
                480                 485                 490 aat ggt aca gtt gat tcc ttt ctg cta gga cca ggt gaa gta agt gta         1841
Asn Gly Thr Val Asp Ser Phe Leu Leu Gly Pro Gly Glu Val Ser Val
            495                 500                 505 tgg cag cat ata agt gaa agt ggt tcc gct cct gtt att ggt caa gta         1889
Trp Gln His Ile Ser Glu Ser Gly Ser Ala Pro Val Ile Gly Gln Val
        510                 515                 520
```

-continued

```
ggc ccg cct atg ggg aaa cct gga gat gct gtg aag att agt ggc agc      1937
Gly Pro Pro Met Gly Lys Pro Gly Asp Ala Val Lys Ile Ser Gly Ser
    525                 530                 535 gga ttt ggt tct gag cct ggc acc gtg tac ttc aga gat acg aaa ata      1985
Gly Phe Gly Ser Glu Pro Gly Thr Val Tyr Phe Arg Asp Thr Lys Ile
540                 545                 550                 555 gac gtg tta act tgg gat gat gaa acg att gtg atc aca ctg ccg gaa      2033
Asp Val Leu Thr Trp Asp Asp Glu Thr Ile Val Ile Thr Leu Pro Glu
                560                 565                 570 aca tta gga gga aaa gcg caa atc agt gtt act aac tct gac ggc gtg      2081
Thr Leu Gly Gly Lys Ala Gln Ile Ser Val Thr Asn Ser Asp Gly Val
            575                 580                 585 aca agt aac ggc tat gat ttt cag ttg ttg aca ggt aag cag gaa tct      2129
Thr Ser Asn Gly Tyr Asp Phe Gln Leu Leu Thr Gly Lys Gln Glu Ser
        590                 595                 600 gtt cgt ttc gtt gtg gat aat gcg cat acc aat tat ggg gaa aat gtt      2177
Val Arg Phe Val Val Asp Asn Ala His Thr Asn Tyr Gly Glu Asn Val
    605                 610                 615 tat ctt gtt gga aat gtt cct gag ctt ggg aat tgg aac cct gcc gac      2225
Tyr Leu Val Gly Asn Val Pro Glu Leu Gly Asn Trp Asn Pro Ala Asp
620                 625                 630                 635 gca atc gga cca atg ttt aat caa gtc gtt tat tcc tat cca acc tgg      2273
Ala Ile Gly Pro Met Phe Asn Gln Val Val Tyr Ser Tyr Pro Thr Trp
                640                 645                 650 tat tac gat gtc agt gtt ccc gcg gat acc gcg ttg gaa ttt aag ttt      2321
Tyr Tyr Asp Val Ser Val Pro Ala Asp Thr Ala Leu Glu Phe Lys Phe
            655                 660                 665 att att gtc gat gga aat gga aat gtt act tgg gaa agc ggg ggt aat      2369
Ile Ile Val Asp Gly Asn Gly Asn Val Thr Trp Glu Ser Gly Gly Asn
        670                 675                 680 cac aat tat cgt gtt acc tcg gga agc acg gat act gtt cgt gta agt      2417
His Asn Tyr Arg Val Thr Ser Gly Ser Thr Asp Thr Val Arg Val Ser
    685                 690                 695 ttt cga agg taaacgaatc tttgggtacc tgattataga agtgtttgtt              2466
Phe Arg Arg
700 caaaaagatt gctttttatc tttttgaaca aacacgagat gatgaaatga gtagagccga    2526 tgca                                                                 2530
```

<210> SEQ ID NO 2
<211> LENGTH: 702
<212> TYPE: PRT
<213> ORGANISM: Bacillus clarkii
<220> FEATURE:
<223> OTHER INFORMATION: 7364

<400> SEQUENCE: 2

```
Val Phe Arg Lys Leu Leu Cys Thr Leu Val Thr Ile Ile Thr Leu Ser
  1               5                  10                  15

Ala Trp Ile Val Ser His Gly Gly Glu Val His Ala Ser Asn Ala Thr
             20                  25                  30

Asn Asp Leu Ser Asn Val Asn Tyr Ala Glu Glu Val Ile Tyr His Ile
         35                  40                  45

Val Thr Asp Arg Phe Lys Asp Gly Asp Pro Asp Asn Asn Pro Gln Gly
     50                  55                  60

Gln Leu Phe Ser Asn Gly Cys Ser Asp Leu Thr Lys Tyr Cys Gly Gly
 65                  70                  75                  80

Asp Trp Gln Gly Ile Ile Asp Glu Ile Glu Ser Gly Tyr Leu Pro Asp
```

-continued

```
                    85                  90                  95
Met Gly Ile Thr Ala Leu Trp Ile Ser Pro Val Glu Asn Val Phe
                    100                 105                 110
Asp Leu His Pro Glu Gly Phe Ser Ser Tyr His Gly Tyr Trp Ala Arg
            115                 120                 125
Asp Phe Lys Lys Thr Asn Pro Phe Gly Asp Phe Asp Asp Phe Ser
    130                 135                 140
Arg Leu Ile Glu Thr Ala His Ala His Asp Ile Lys Val Val Ile Asp
145                 150                 155                 160
Phe Val Pro Asn His Thr Ser Pro Val Asp Ile Glu Asp Gly Ala Leu
                165                 170                 175
Tyr Asp Asn Gly Thr Leu Leu Gly His Tyr Ser Thr Asp Ala Asn Asn
                180                 185                 190
Tyr Phe Tyr Asn Tyr Gly Gly Ser Asp Phe Ser Asp Tyr Glu Asn Ser
            195                 200                 205
Ile Tyr Arg Asn Leu Tyr Asp Leu Ala Ser Leu Asn Gln Gln His Ser
    210                 215                 220
Phe Ile Asp Lys Tyr Leu Lys Glu Ser Ile Gln Leu Trp Leu Asp Thr
225                 230                 235                 240
Gly Ile Asp Gly Ile Arg Val Asp Ala Val His Met Pro Leu Gly
                245                 250                 255
Trp Gln Lys Ala Phe Ile Ser Ser Val Tyr Asp Tyr Asn Pro Val Phe
                260                 265                 270
Thr Phe Gly Glu Trp Phe Thr Gly Ala Gln Gly Ser Asn His Tyr His
            275                 280                 285
His Phe Val Asn Asn Ser Gly Met Ser Ala Leu Asp Phe Arg Tyr Ala
    290                 295                 300
Gln Val Ala Gln Asp Val Leu Arg Asn Gln Lys Gly Thr Met His Asp
305                 310                 315                 320
Ile Tyr Asp Met Leu Ala Ser Thr Gln Leu Asp Tyr Glu Arg Pro Gln
                325                 330                 335
Asp Gln Val Thr Phe Ile Asp Asn His Asp Ile Asp Arg Phe Thr Val
            340                 345                 350
Glu Gly Arg Asp Thr Arg Thr Thr Asp Ile Gly Leu Ala Phe Leu Leu
            355                 360                 365
Thr Ser Arg Gly Val Pro Ala Ile Tyr Tyr Gly Thr Glu Asn Tyr Met
370                 375                 380
Thr Gly Lys Gly Asp Pro Gly Asn Arg Lys Met Met Glu Ser Phe Asp
385                 390                 395                 400
Gln Thr Thr Thr Ala Tyr Gln Val Ile Gln Lys Leu Ala Pro Leu Arg
            405                 410                 415
Gln Glu Asn Lys Ala Val Val Tyr Gly Ser Thr Lys Glu Arg Trp Ile
            420                 425                 430
Asn Asp Asp Val Leu Ile Tyr Glu Arg Ser Phe Asn Gly Asp Tyr Leu
        435                 440                 445
Leu Val Ala Ile Asn Lys Asn Val Asn Gln Ala Tyr Thr Ile Ser Gly
    450                 455                 460
Leu Leu Thr Glu Met Pro Ala Gln Val Tyr His Asp Val Leu Asp Ser
465                 470                 475                 480
Leu Leu Asp Gly Gln Ser Leu Ala Val Lys Glu Asn Gly Thr Val Asp
                485                 490                 495
Ser Phe Leu Leu Gly Pro Gly Glu Val Ser Val Trp Gln His Ile Ser
            500                 505                 510
```

-continued

```
Glu Ser Gly Ser Ala Pro Val Ile Gly Gln Val Gly Pro Pro Met Gly
            515                 520                 525
Lys Pro Gly Asp Ala Val Lys Ile Ser Gly Ser Gly Phe Gly Ser Glu
        530                 535                 540
Pro Gly Thr Val Tyr Phe Arg Asp Thr Lys Ile Asp Val Leu Thr Trp
545                 550                 555                 560
Asp Asp Glu Thr Ile Val Ile Thr Leu Pro Glu Thr Leu Gly Gly Lys
                565                 570                 575
Ala Gln Ile Ser Val Thr Asn Ser Asp Gly Val Thr Ser Asn Gly Tyr
            580                 585                 590
Asp Phe Gln Leu Leu Thr Gly Lys Gln Glu Ser Val Arg Phe Val Val
        595                 600                 605
Asp Asn Ala His Thr Asn Tyr Gly Glu Asn Val Tyr Leu Val Gly Asn
    610                 615                 620
Val Pro Glu Leu Gly Asn Trp Asn Pro Ala Asp Ala Ile Gly Pro Met
625                 630                 635                 640
Phe Asn Gln Val Val Tyr Ser Tyr Pro Thr Trp Tyr Tyr Asp Val Ser
                645                 650                 655
Val Pro Ala Asp Thr Ala Leu Glu Phe Lys Phe Ile Ile Val Asp Gly
            660                 665                 670
Asn Gly Asn Val Thr Trp Glu Ser Gly Gly Asn His Asn Tyr Arg Val
        675                 680                 685
Thr Ser Gly Ser Thr Asp Thr Val Arg Val Ser Phe Arg Arg
    690                 695                 700
```

<210> SEQ ID NO 3
<211> LENGTH: 22
<212> TYPE: PRT
<213> ORGANISM: Bacillus clarkii
<220> FEATURE:
<223> OTHER INFORMATION: 7364

<400> SEQUENCE: 3

```
Ser Asn Ala Thr Asn Asp Leu Ser Asn Val Asn Tyr Ala Glu Glu
 1               5                  10                  15
Val Ile Tyr His Ile Val Thr
                20
```

<210> SEQ ID NO 4
<211> LENGTH: 27
<212> TYPE: PRT
<213> ORGANISM: Bacillus clarkii
<220> FEATURE:
<223> OTHER INFORMATION: 7364

<400> SEQUENCE: 4

```
Ser Glu Ser Gly Ser Ala Pro Val Ile Gly Gly Pro Pro Met Gly
 1               5                  10                  15
Lys Pro Gly Asp Ala Val Lys Ile Ser Gly Ser Gly
                20                  25
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)

```
<223> OTHER INFORMATION: Inosine
<220> FEATURE:
<221> NAME/KEY: modified_base
<222> LOCATION: (9)
<223> OTHER INFORMATION: Inosine
<220> FEATURE:
<221> NAME/KEY: modified_base
<222> LOCATION: (15)
<223> OTHER INFORMATION: Inosine

<400> SEQUENCE: 5
aaygtnaant aygcngarga rgt                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: Inosine
<220> FEATURE:
<221> NAME/KEY: modified_base
<222> LOCATION: (9)
<223> OTHER INFORMATION: Inosine
<220> FEATURE:
<221> NAME/KEY: modified_base
<222> LOCATION: (15)
<223> OTHER INFORMATION: Inosine

<400> SEQUENCE: 6
gcrtcnccng gyttncccat dcc                                              23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
gatctgttac aatatgataa at                                               22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ttattagacg gtcaatcgtt a                                                21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Pimer

<400> SEQUENCE: 9
gacttgtact aagacaacct tacg                                             24

<210> SEQ ID NO 10
<211> LENGTH: 21
<212> TYPE: DNA
<213> ORGANISM: Artificial Sequence
```

-continued

```
<220> FEATURE:
<223> OTHER INFORMATION: Description of Artificial Sequence: Pimer

<400> SEQUENCE: 10
gcatcggctc tactcatttc a                                            21
```